United States Patent
Bolea et al.

(10) Patent No.: US 10,422,753 B2
(45) Date of Patent: Sep. 24, 2019

(54) LIGHT DETECTION SYSTEM AND METHOD OF USING SAME

(71) Applicant: 3M INNOVATIVE PROPERTIES COMPANY, Saint Paul, MN (US)

(72) Inventors: Phillip A. Bolea, Grant, MN (US); Giuseppe M. Bommarito, Stillwater, MN (US); Michele A. Waldner, Minneapolis, MN (US); Thomas J. Brace, Saint Paul, MN (US); Stephen R. Alexander, Stillwater, MN (US); Thomas E. Dewey, Jr., Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 135 days.

(21) Appl. No.: 15/557,908

(22) PCT Filed: Mar. 10, 2016

(86) PCT No.: PCT/US2016/021673
§ 371 (c)(1),
(2) Date: Sep. 13, 2017

(87) PCT Pub. No.: WO2016/149017
PCT Pub. Date: Sep. 22, 2016

(65) Prior Publication Data
US 2018/0113076 A1   Apr. 26, 2018

Related U.S. Application Data
(60) Provisional application No. 62/132,774, filed on Mar. 13, 2015.

(51) Int. Cl.
*G01N 21/76* (2006.01)
*G01J 1/42* (2006.01)
(Continued)

(52) U.S. Cl.
CPC ............ *G01N 21/763* (2013.01); *C12Q 1/008* (2013.01); *C12Q 1/66* (2013.01); *G01J 1/0295* (2013.01);
(Continued)

(58) Field of Classification Search
CPC .... G01N 21/763; G01J 1/0295; G01J 1/0411; G01J 1/0418; G01J 1/08; G01J 1/42
See application file for complete search history.

(56) References Cited

U.S. PATENT DOCUMENTS
4,422,761 A * 12/1983 Frommer ............... G01N 21/47
356/246
4,755,055 A    7/1988 Johnson et al.
(Continued)

FOREIGN PATENT DOCUMENTS
DE    198 40 055    3/2000
GB    2 223 095     3/1990
(Continued)

OTHER PUBLICATIONS
Brochure entitled "3M™ Clean-Trace™ System—More reliable, ATP tests" from 3M Company; 2007; 2 pgs.

*Primary Examiner* — David P Porta
*Assistant Examiner* — Jeremy S Valentiner
(74) *Attorney, Agent, or Firm* — Eric E. Silverman (57) ABSTRACT

Various embodiments of a light detection device and a system that utilizes such device are disclosed. In one or more embodiments, the light detection device can include a housing that includes a port disposed in a top surface, a receptacle disposed within the housing and adapted to receive a sample, a detector disposed within the housing along an optical axis and including an input surface having an active area, and a reflector disposed within the housing along the optical axis between the receptacle and the input surface of the detector.

(Continued)

The reflector can include an input aperture disposed adjacent the receptacle, an output aperture disposed adjacent the input surface of the detector, and a reflective surface that extends between the input aperture and the output aperture.

19 Claims, 5 Drawing Sheets

(51) Int. Cl.

| | | |
|---|---|---|
| *G01N 21/03* | (2006.01) | |
| *G01J 1/02* | (2006.01) | |
| *C12Q 1/00* | (2006.01) | |
| *C12Q 1/66* | (2006.01) | |
| *G01N 33/573* | (2006.01) | |
| *G01N 33/68* | (2006.01) | |
| *G01J 1/04* | (2006.01) | |
| *G01J 1/08* | (2006.01) | |
| *G01J 3/42* | (2006.01) | |
| *G01N 21/94* | (2006.01) | |

(52) U.S. Cl.
CPC ........... *G01J 1/0411* (2013.01); *G01J 1/0418* (2013.01); *G01J 1/08* (2013.01); *G01J 1/42* (2013.01); *G01J 3/42* (2013.01); *G01N 21/0303* (2013.01); *G01N 33/573* (2013.01); *G01N 33/6863* (2013.01); *G01N 21/94* (2013.01); *G01N 2021/0325* (2013.01); *G01N 2201/0221* (2013.01); *G01N 2201/064* (2013.01); *G01N 2201/065* (2013.01)

(56) References Cited

U.S. PATENT DOCUMENTS

| | | | |
|---|---|---|---|
| 5,086,233 A | | 2/1992 | Stafford et al. |
| 5,526,022 A | * | 6/1996 | Donahue .................. G01C 9/20 324/253 |
| 5,827,675 A | | 10/1998 | Skiffington et al. |
| 6,055,050 A | | 4/2000 | Skiffington |
| 6,197,254 B1 | | 3/2001 | Silver et al. |
| 7,981,362 B2 | | 7/2011 | Glezer et al. |
| 2003/0119030 A1 | | 6/2003 | Zilber |
| 2004/0149899 A1 | | 8/2004 | Packman et al. |
| 2004/0220748 A1 | | 11/2004 | Feldsine et al. |
| 2005/0089995 A1 | | 4/2005 | Jones |
| 2006/0166371 A1 | | 7/2006 | Testa et al. |
| 2006/0216196 A1 | | 9/2006 | Satoh et al. |
| 2007/0257202 A1 | | 11/2007 | Walker |
| 2008/0261294 A1 | * | 10/2008 | Noda ..................... G01N 21/76 435/286.2 |
| 2010/0068750 A1 | | 3/2010 | Pogosjan et al. |
| 2010/0129840 A1 | | 5/2010 | Charm et al. |
| 2011/0143947 A1 | | 6/2011 | Chamberlin et al. |
| 2012/0135511 A1 | | 5/2012 | Battrell et al. |
| 2012/0329081 A1 | | 12/2012 | Bennion et al. |
| 2014/0004548 A1 | * | 1/2014 | Gordon ................ B01L 3/5029 435/21 |
| 2014/0038199 A1 | * | 2/2014 | Percy ..................... G01N 21/03 435/6.12 |
| 2014/0154792 A1 | | 6/2014 | Moynihan et al. |
| 2014/0273189 A1 | * | 9/2014 | Ma ........................ G01J 3/0291 435/287.2 |

FOREIGN PATENT DOCUMENTS

| | | |
|---|---|---|
| GB | 2 281 966 | 3/1995 |
| JP | 2009-264821 | 11/2009 |
| WO | WO 1996/14570 | 5/1996 |
| WO | WO 1997/03209 | 1/1997 |
| WO | WO 1998/49544 | 11/1998 |
| WO | WO 1998/54578 | 12/1998 |
| WO | WO 2014/001982 | 1/2014 |
| WO | WO 2014/007846 | 1/2014 |
| WO | WO 2016/148867 | 9/2016 |
| WO | WO 2016/148922 | 9/2016 |

* cited by examiner

LIGHT DETECTION SYSTEM AND METHOD OF USING SAME

CROSS REFERENCE TO RELATED APPLICATIONS

This application is a national stage filing under 35 U.S.C. 371 of PCT/US2016/021673, filed Mar. 10, 2016, which claims the benefit of U.S. Provisional Application No. 62/132,774, filed Mar. 13, 2015, the disclosures of which are incorporated by reference in their entirety herein.

BACKGROUND

Sampling programs are used to monitor critical raw materials, in-process materials, finished goods, and processing environments in the food and beverage industry. Similar sampling programs are also used in healthcare settings to monitor the effectiveness of decontaminating environmental surfaces in a patient environment as well as instruments and devices used in screening and therapeutic procedures. Routine sampling and testing can allow quality assurance personnel to detect undesirable materials, such as microorganisms, at a very early stage and take steps to prevent subsequent contamination of equipment and/or products. A variety of tests can be performed to detect these undesirable materials. Examples of such tests include chemical residue tests (e.g., Adenosine triphosphate (ATP) bioluminescence tests and protein colorimetric tests), culture methods, genetic tests (e.g., PCR), immunodiagnostic tests, and bioluminescent tests.

Sample-collection devices or apparatuses are typically used to collect surface samples for environmental tests. Commercially-available sample-collection devices include absorbent devices such as sponges, swabs, and the like. In addition, certain sample-collection devices are capable of collecting a predetermined volume of a liquid sample.

Because of its use as energy "currency" in all metabolizing systems, ATP can indicate the presence of organic or bioorganic residues in a sample. The presence of ATP can be measured using a bioluminescent enzymatic assay. For example, a luciferin/luciferase enzyme assay system uses ATP to generate light. This light output can be detected and quantified in a light detection device, e.g., a luminometer. The presence of ATP in a sample may be a direct indicator of the presence of a microorganism (i.e., the ATP is derived from microorganisms in a sample containing no other sources of ATP), or the ATP may be an indirect indicator of the presence of a microorganism (i.e., the ATP is derived from vegetative or animal matter and indicates that nutrients that support the growth of microorganisms may be present in the sample). In addition, the presence or absence of ATP in a sample is used routinely to assess the efficacy of cleaning processes, e.g., in food, beverage, healthcare (e.g., environmental surfaces, surgical instruments, endoscopes, and other medical devices), water, and sanitation industries.

For example, ATP measurement systems have been utilized as monitoring tools in the food industry for over 15 years to audit the efficacy of sanitation processes. Such systems can detect very small amounts of ATP (e.g., 1 femtomole) on a variety of surfaces commonly found in food processing operations that need to be cleaned and disinfected. Detecting the presence of ATP on surfaces that are supposed to be sanitized can indicate a failure of the cleaning and disinfection process.

More recently, ATP monitoring tools have been adopted for a similar purpose in clinical applications to monitor the cleanliness of a patient's environment. There is now compelling clinical evidence that contaminated surfaces in a hospital make an important contribution to the epidemic and endemic transmission, e.g., of *C. difficile*, VRE, MRSA, *A. baumannii*, and *P. aeruginosa*, and to the endemic transmission of norovirus. Effective infection prevention programs include systematic monitoring of the environment's cleanliness. ATP monitoring, for example, can provide a quantitative measurement system that can be used to support such a program.

SUMMARY

In general, the present disclosure provides various embodiments of a light detection device and a system that utilizes the detection device. The light detection device can include a housing, a receptacle disposed within the housing, and a detector also disposed within the housing. The light detection device can also include a reflector disposed within the housing between a second end of the receptacle and an input surface of the detector. In one or more embodiments, a cross-sectional area of an output aperture of the reflector can be no greater than an active area of the input surface of the detector.

In one aspect, the present disclosure provides a light detection device that includes a housing extending along a housing axis between a top surface and a bottom surface, where the housing includes a port disposed in the top surface, and where the port includes an opening. The light detection device also includes a receptacle disposed within the housing and adapted to receive a sample, where the receptacle includes a receptacle body extending along an optical axis, the receptacle body including a first end connected to the opening of the port of the housing and a second end. The light detection device also includes a detector disposed within the housing along the optical axis and includes an input surface adjacent the second end of the receptacle body, where the input surface includes an active area. Further, the light detection device also includes a reflector disposed within the housing along the optical axis between the second end of the receptacle body and the input surface of the detector, where the reflector includes an input aperture disposed adjacent the second end of the receptacle body, an output aperture disposed adjacent the input surface of the detector, and a reflective surface that extends between the input aperture and the output aperture. Further, a cross-sectional area of the output aperture of the reflector is no greater than a surface area of the active area of the input surface of the detector.

In another aspect, the present disclosure provides a method that includes disposing a bioluminescent sample within a receptacle of a light detection device, where the receptacle includes a receptacle body extending along an optical axis. The receptacle body includes a first end and a second end. The method further includes disposing a detector along the optical axis, where the detector includes an input surface. The method further includes disposing a reflector along the optical axis between the second end of the receptacle body and an input surface of a detector, where the reflector includes an input aperture disposed adjacent the second end of the receptacle body, an output aperture disposed adjacent the input surface of the detector, and a reflective surface that extends between the input aperture and the output aperture. The reflector and the input surface of the detector form a light cavity. The method further includes directing light emitted into the light cavity by the bioluminescent sample through an active area of the input surface of the detector, where a cross-sectional area of the output aperture of the reflector is no greater than a surface area of the active area of the input surface of the detector. Further, the method includes measuring a characteristic of the emitted light using the detector.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise. The use of the term "and/or" in certain portions of this disclosure is not intended to mean that the use of "or" in other portions cannot mean "and/or."

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

In general, the present disclosure provides various embodiments of a light detection device and a system that utilizes the detection device. The light detection device can include a housing, a receptacle disposed within the housing, and a detector also disposed within the housing. The light detection device can also include a reflector disposed within the housing between a second end of the receptacle and an input surface of the detector. In one or more embodiments, a cross-sectional area of an output aperture of the reflector can be no greater than an active area of the input surface of the detector.

The light detection device can be utilized in any suitable application. For example, the light detection device can be utilized to detect and measure light emitted by a bioluminescent sample disposed within the device. The bioluminescent sample can include any suitable sample. In one or more embodiments, the bioluminescent sample can produce light from a luciferin-luciferase enzymatic reaction to detect and quantify the presence of ATP from various environmental samples.

The accuracy and repeatability of currently available ATP detection systems can vary significantly. Such variability can be caused by difficulties in acquiring samples in a repeatable manner. Further, systems that employ a luciferin-luciferase detection chemistry can vary because of the lack of repeatability of how the reagent composition is formulated and the form factor employed to provide the reagents in an assay. In addition, the optical characteristics of the detection system can affect accuracy and repeatability. For example, a detection system can include a reflector, detector, and a sample chamber or cuvette portion containing a sample, which form an optical train that can have different designs, configurations and alignments. Further, all systems create a user experience that affects not only the ease of use of the system but also its overall performance.

One or more embodiments of the present disclosure can advantageously optimize the capture efficiency of the light emitted by a sample, thereby providing enhanced overall sensitivity and an increase in robustness of the system with respect to accuracy and reproducibility. Further, one or more embodiments can include a receptacle disposed within a housing of a light detection device that can prevent a sample disposed therein from leaking into circuitry and/or a detector disposed within the housing.

FIGS. 1-5 are various views of one embodiment of a light detection system 2. The system 2 can include a light detection device 10 and a sampling apparatus (not shown), e.g. sampling apparatus 80 of FIG. 6. The light detection device 10 can include any suitable light detection device adapted for detecting light emitted by a sample disposed within the device, e.g., a luminometer. The light detection device 10 can be a handheld device that is portable. In one or more embodiments, the light detection device 10 can be a benchtop device for use in a lab.

Figure 1:
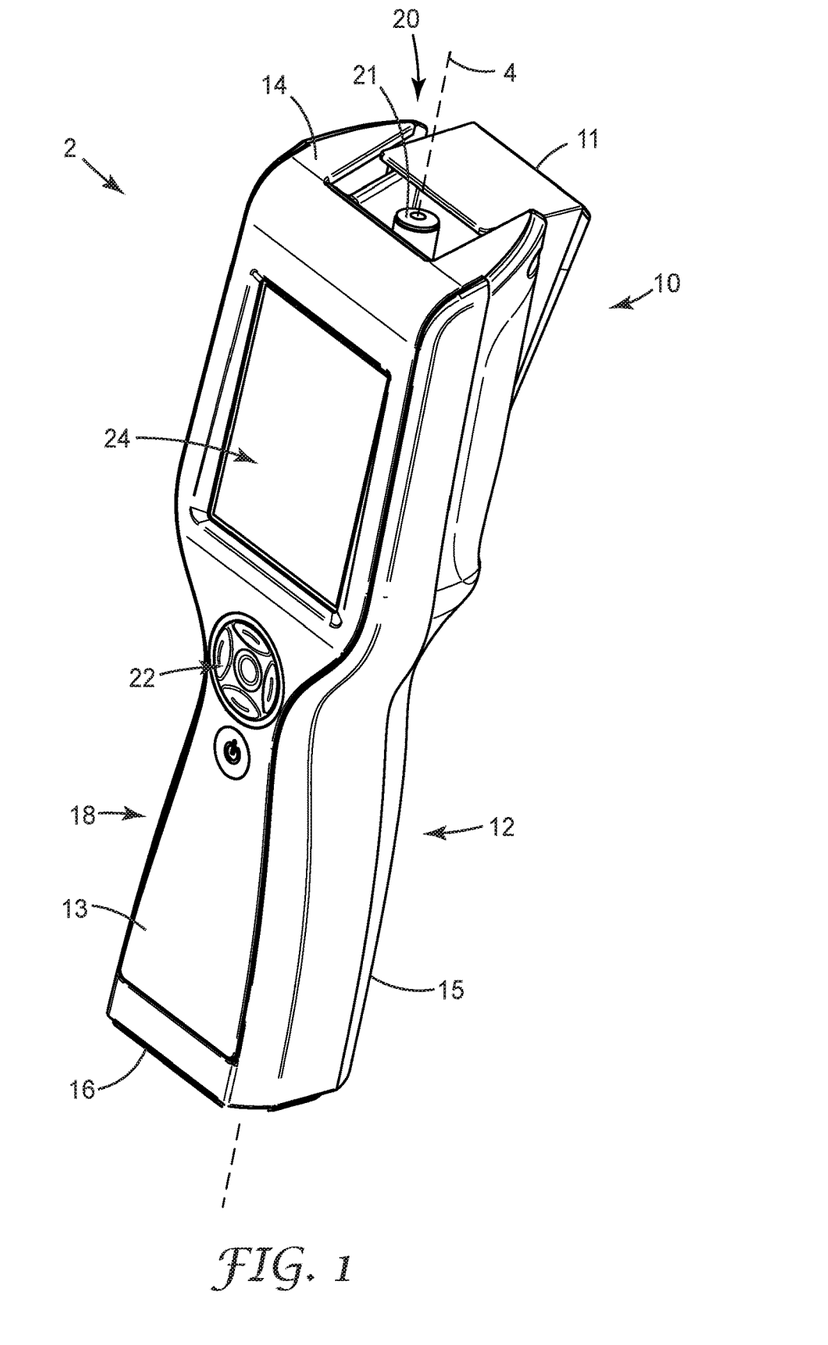
FIG. 1 is a schematic perspective view of one embodiment of a light detection system.
Figure 2:
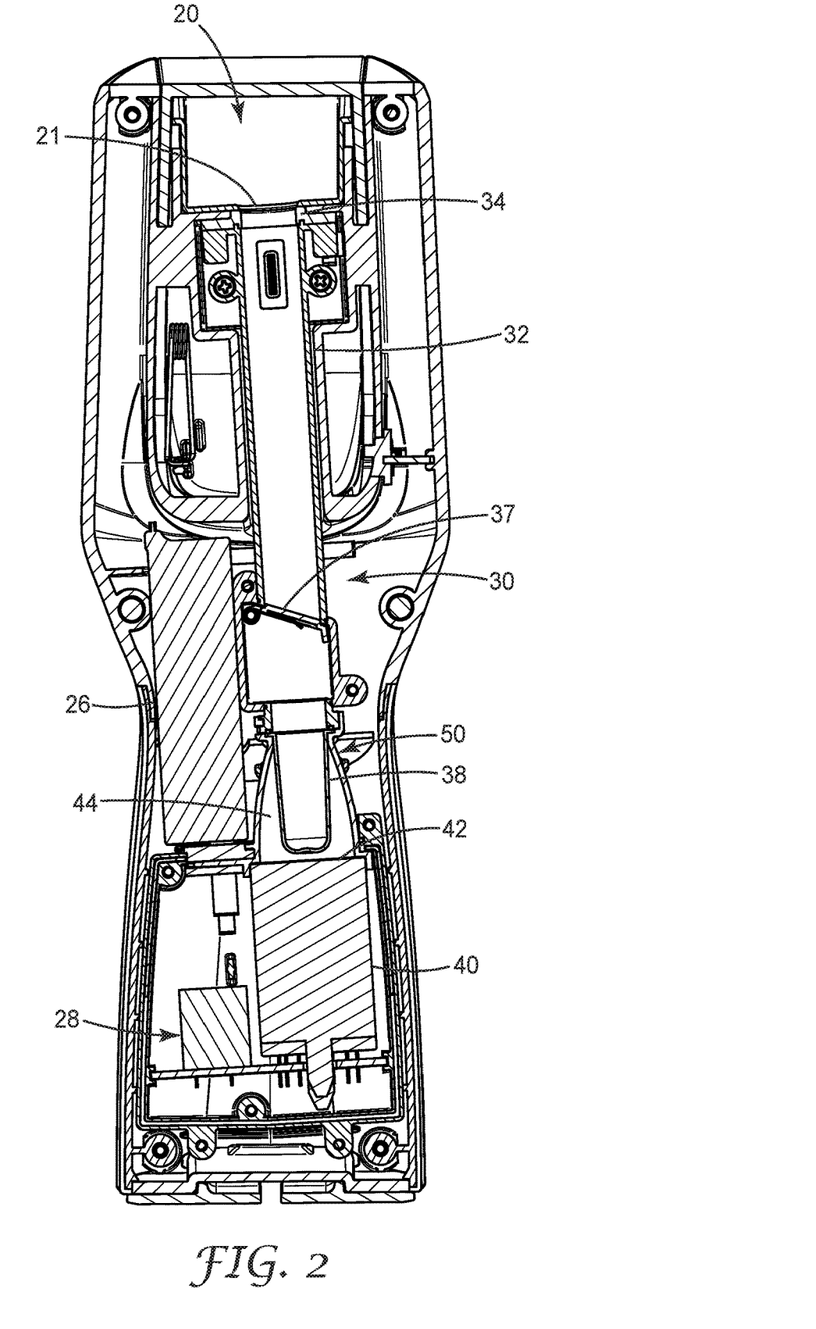
FIG. 2 is a schematic cross-section of a light detection device of the light detection system of FIG. 1.

The device 10 can include a housing 12. The housing 12 can take any suitable shape or combination of shapes.

Further, the housing can include any suitable material or combination of materials. The housing 12 can extend along a housing axis 4 from a top surface 14 to a bottom surface 16. The housing 12 can also include a handle portion 18 disposed between the top surface 14 and the bottom surface 16. Further, the housing 12 can be a single, unitary housing or can include several portions that are attached using any suitable technique or combination of techniques e.g., screws, adhesives, tabs, etc. In one or more embodiments, the housing 12 can take an ergonomic shape or combination of shapes to allow a user to grasp the housing and operate the device 10 with a single hand.

The housing 12 can also include a port 20 disposed in the top surface 14 of the housing. Although illustrated as being disposed in the top surface 14, the port 20 can be disposed in any suitable surface of the housing 12, e.g., in the bottom surface 16, in a front surface 13, or in a back surface 15 of the housing. The port 20 can be adapted to receive a sampling apparatus (e.g., sampling apparatus 80 of FIG. 6). The port 20 can take any suitable shape or combination of shapes. The port 20 can include an opening 21 formed in the port along the housing axis 4. The opening 21 can take any suitable shape or combination of shapes and include any suitable dimensions. In one or more embodiments, the opening 21 can be adapted to receive a sample. Further, in one or more embodiments, the opening 21 can be adapted to receive a sampling apparatus as is further described herein.

In one or more embodiments, the housing 12 can also include a door 11 that is adapted to cover the port 20 to prevent ambient light from entering the housing. Any suitable door 11 can be utilized, e.g., the doors described in co-filed U.S. Provisional Patent Application Ser. No. 62/132, 790, filed Mar. 13, 2015. The door 11 can be attached to the housing 12 using any suitable technique or combination of techniques, e.g., with a hinge. Further, the door 11 can be attached to the housing 12 in any suitable location such that it is adapted to close the port 20. In one or more embodiments, the door 11 can be removable from the housing 12 such that the door is a separate component.

Although not shown in FIG. 1, the port 20 can also include a ledge and one or more gaskets that can engage the door 11 and provide a sealed port to prevent ambient light from entering the housing when the door is in a closed position. The housing 12 can include any type of additional ports, e.g., communication or electrical ports, that provide the ability to connect the device 10 to any suitable external devices, e.g., power supplies, computers, memory devices, etc.

The light detection device 10 can also include one or more controls 22 that are adapted to provide an interface for the user to perform various functions with the device. Any suitable control or controls 22 can be provided with the device 10. Further, in one or more embodiments, the controls 22 can be disposed in any suitable location on or in the housing 12. For example, in the embodiment illustrated in FIG. 1, the controls 22 are disposed such that a user can grasp the handle portion 18 of the housing 12 and operate the controls with a thumb or finger of the grasping hand. Such positioning of the controls 22 allows use of the device 10 with a single hand. The controls 22 can be electrically coupled to any suitable circuitry 28 disposed within the housing 12 of the device 10. Such circuitry 28 can include any suitable electronic device or devices, e.g., one or more controllers, processors, storage devices, power converters, analog/digital converters, GPS components, wireless antennas and receivers, etc. The circuitry 28 can be electrically coupled to any suitable power source or sources, e.g., battery 26, external power sources, etc.

The device 10 can also include a display 24 that is adapted to provide a user interface with the circuitry 28 disposed within the housing 12 of the device. The display 24 can include any suitable display. In one or more embodiments, the display 24 can be a touch sensitive display that provides control of the device to a user and also displays information to the user. Any suitable touch-sensitive display 24 can be utilized with device 10.

Figure 3:
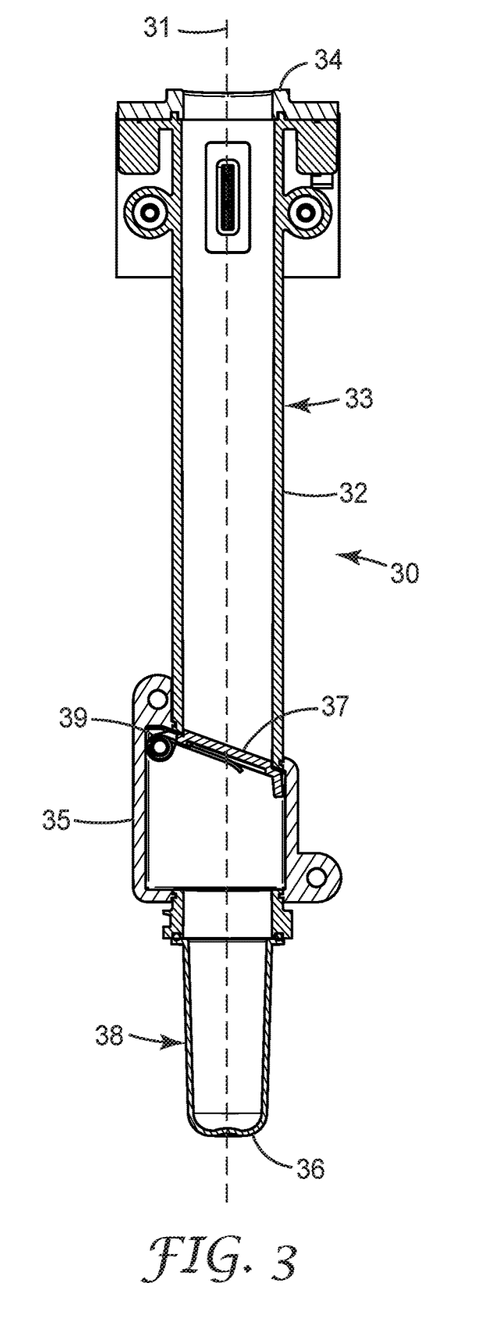
FIG. 3 is a schematic cross-section view of a receptacle of the light detection device of FIG. 2.

Also, disposed within the housing 12 of the device 10 is a receptacle 30 as shown in FIGS. 2-3. In one or more embodiments, the receptacle 30 is adapted to receive a sampling apparatus, e.g., sampling apparatus 80 of FIG. 6. Further, in one or more embodiments, a sample may be disposed directly in the receptacle without the use of the sampling apparatus. In general, the receptacle 30 can be adapted such that it guides the sampling apparatus into the housing 12 of the light detection device 10. The receptacle 30 can include a receptacle body 32 that extends along an optical axis 31. The receptacle body 32 can include a first end 34 connected to the opening 21 of the port 20 of the housing 12, and a second end 36. In one or more embodiments, the receptacle body 32 can also include an optional transmissive region 38 that is disposed adjacent the second end 36 of the body. As used herein, the phrase "adjacent the second end" means that the transmissive region 38 is disposed such that it is closer to the second end 36 of the body 32 than to the first end 34. Although illustrated in FIGS. 2-3 as including the transmissive region 38, the receptacle body 32 can instead include an opening at the second end 36 and no transmissive region. In such embodiments, a sampling apparatus can be disposed within the receptacle 30 such that a cuvette portion of the apparatus that contains a sample extends beyond the body 32 at the second end 36.

The receptacle 30 can be disposed within the housing 12 of the device 10 in any suitable location and in any suitable orientation. In general, the receptacle 30 is adapted and disposed within the housing 12 such that a sampling apparatus is properly oriented in relation to a detector 40 that is disposed adjacent the second end 36 of the receptacle body 32. For example, the receptacle 30 can be disposed such that the optical axis 31 forms any suitable angle with housing axis 4. For example, the optical axis 31 can be substantially parallel with the housing axis 4. As used herein, the term "substantially parallel with the housing axis" means that the optical axis 31 forms an angle with the housing axis 4 that is no greater than 10 degrees. Further, for example, the optical axis 31 can be collinear with the housing axis 4.

In one or more embodiments, the receptacle 30 can be disposed within the housing 12 such that the angle between the optical axis 31 and a vertical axis when the device is held in an operational position is selected to maximize the signal output from the detector during testing. As used herein, the term "vertical axis" refers to an axis that is aligned with the Earth's gravitational field. In one or more embodiments, the angle between the optical axis 31 and the vertical axis is in a range of 0° to 45°. In one or more embodiments, the angle between the optical axis 31 and the vertical axis is in a range of 0° to 30°.

The first end 34 of the receptacle body 32 can be connected to the opening 21 of the port 20 using any suitable technique or combination of techniques. In one or more embodiments, the first end 34 of the receptacle body 32 can be sealed to the opening 21 of the port 20 to prevent light or external environmental elements from entering the interior of the housing 12 through any gap or space between the receptacle and the port 20. In one or more embodiments, the receptacle body 32 can be integral with the port 20, e.g., the port and the receptacle body can be manufactured out of a single piece or molded into a single piece. In one or more embodiments, the port 20 can be manufactured separately from the receptacle body 32 such that the receptacle 30 can be removed from the housing and repaired, clean, or replaced.

The receptacle body 32 can include any suitable material or combination of materials. In one or more embodiments, an upper region 33 of the receptacle body 32 can include a material or combination of materials such that the upper region is opaque. In one or more embodiments, the upper region 33 can include a material or combination of materials that is reflective or light absorbing. In one or more embodiments, a first portion of the upper region 33 can be reflective and a second portion can be light absorbing.

The optional transmissive region 38 of the receptacle body 32 can include any suitable material or combination of materials such that the transmissive region transmits at least a portion of light emitted by a sample disposed within the receptacle 30. Further, the transmissive region 38 can be a transmissive cup that is connected to the second end 36 of the receptacle body 32 using any suitable technique or combination of techniques. In one or more embodiments, the materials and/or configuration of the transmissive region 38 can be adapted such that it transmits broadband light, e.g., at least one of ultraviolet, visible, and infrared light. In one or more embodiments, the transmissive region 38 can be adapted such that it transmits a narrow band of light, e.g., only ultraviolet light. Further, in one or more embodiments, the transmissive region 38 can be adapted such that it transmits a narrow band of visible light, e.g., blue light. The transmissive region 38 can also be adapted such that light emitted by the sample disposed within the receptacle 30 is directed toward the detector 40 disposed adjacent the second end 36 of the receptacle 30 as is further described herein.

The upper region 33 and the transmissive region 38 of the receptacle body 32 can be unitary. In one or more embodiments, the upper region 33 can be attached to the transmissive region 38 such that the upper region and the transmission region are manufactured separately and attached using any suitable technique or combination of techniques.

In one or more embodiments, the receptacle body 32 is adapted to enclose a sample disposed within the receptacle and prevent the sample from leaking out of the body and into the interior of the housing 12 of the device 10. Such leakage could cause damage to the internal circuitry 28 of the device 10 and to the detector 40. In other words, the receptacle 30 can be adapted to provide a contamination barrier between the detector 40 and a sample disposed within the receptacle.

As mentioned herein, the receptacle 30 can be permanently disposed within the housing 12. In one or more embodiments, the receptacle 30 can be disposed within the housing 12 such that it is removable. To remove the receptacle 30, the housing 12 can include one or more portions or parts that are attached using any suitable technique such that the surfaces can be separated, thereby providing access to the interior of the housing 12. Once the interior of the housing 12 is exposed, the receptacle 30 can be removed and either cleaned, repaired, or replaced.

The receptacle 30 can also include a shutter 37 disposed within the receptacle body 32. The shutter 37 can be disposed in any suitable location within the receptacle body 32 such that the shutter prevents ambient light from entering the detector 40 and potentially causing damage to the detector when a sample (e.g., disposed within a sampling apparatus) is not present. In one or more embodiments, the shutter 37 is adapted to be displaced by a sampling apparatus when the sampling apparatus is inserted into the receptacle 30 through the opening 21 of the port 20. In one or more embodiments, the shutter 37 is disposed between the first end 34 and the second end 36 of the receptacle body 32. The shutter 37 can include any suitable mechanism that is adapted to prevent light from being directed along the receptacle body 32 and into the detector 40. For example, the shutter 37 can include an electrical, a mechanical, or an electromechanical shutter. As a sampling apparatus is inserted into the receptacle body 32, an end portion of the sampling apparatus (e.g., cuvette portion 100 of sampling apparatus 80 of FIG. 6) presses against the shutter 37, causing the shutter to be displaced and allowing the end portion of the sampling apparatus to be inserted, e.g., into the transmissive region 38 of the body 32.

The shutter 37 can be attached to the receptacle body 32 using any suitable technique or combination of techniques. For example, the shutter 37 can be attached to the receptacle body 32 using a hinge 39. Any suitable hinge can be utilized. In one or more embodiments, the hinge 39 can be spring-loaded such that the hinge 39 is biased in a closed position. When an end portion of a sampling apparatus is pressed against the shutter 37, the shutter is moved from the closed position to an open position, thereby allowing the end portion of the sampling apparatus to be inserted, e.g., into the transmissive region 38 of the receptacle body 32. The receptacle body 32 can include an inset portion 35 that accommodates the shutter 37 when in the open position, e.g., when a sampling apparatus is disposed within the receptacle body.

The shutter 37 can be electrically coupled to a switch that is adapted to activate circuitry 28 utilized to analyze the sample disposed within the receptacle 30. Any suitable switch or combination of switches can be utilized with the shutter 37. In one or more embodiments, the circuitry 28 can prevent the detector 40 from being activated when the shutter 37 is in the closed position. Such a configuration can further prevent damage to the detector 40 from ambient light that enters the housing through the port 20 and the receptacle 30.

The light detection device 10 of light detection system 2 can also include a detector 40 that includes an input surface 42. The detector 40 can include any suitable detection device or combination of devices, e.g., photomultiplier tube, avalanche detector, photodiode, etc. The detector 40 is adapted to receive light emitted by a sample disposed within receptacle 30 and directed through the input surface 42 within an active area of the detector. As used herein, the term "active area" means an area of the input surface 42 through which light can be transmitted into the detector 40 and be detected. Light transmitted through the input surface 42 outside of the active area will not be detected by the detector 40. The active area can include any suitable portion or portions of the input surface 42. In one or more embodiments, a surface area of the active area can be the same as a surface area of the input surface 42, i.e., the active area and the input surface are coincident. In one or more embodiments, the surface area of the active area can be less than a surface area of the input surface 42. Further, the active area can take any suitable shape or combination of shapes and have any suitable dimensions. In one or more embodiments, the active area can take a circular shape. In such embodiments, the active area can have a diameter of at least about 5 mm, 10 mm, 15 mm, 20 mm, 30 mm, 40 mm, etc. In one or more embodiments, the active area can have a diameter of no greater than about 50 mm. The detector 40 can, in one or more embodiments, determine a characteristic of the emitted light, e.g., intensity, flux, wavelength, integrated light, etc. The device 10 can include any suitable number of detectors 40, e.g., one, two, three, or more detectors. The detector 40 can be electrically coupled to circuitry 28.

In operation, photons emitted by the sample strike or are incident upon the input surface 42 of the detector 40. The photons incident on the input surface 42 within the active area such that they are transmitted through the input surface and into the detector can create, e.g., an electrical signal which can be filtered, amplified, and transmitted to circuitry 28. A characteristic (e.g., voltage, current, duty cycle) of the electrical signal provided by the detector 40 can be related to the number of photons emitted by the sample. The number of photons emitted by the sample can, in turn, be proportionate to the amount of biological material present in the sample. The electrical signal generated by the detector 40, therefore, can provide an indication of not only the presence but also the relative quantity of biological material present in the sample. In one or more embodiments, the light output detected by the detector can be characterized in relative light units (RLUs).

Figure 4:
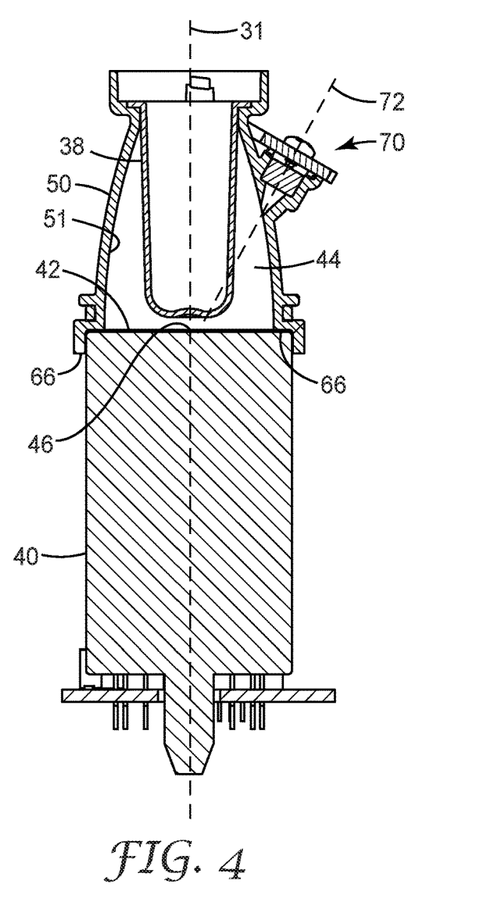
FIG. 4 is a schematic cross-section view of a portion of the light detection device of FIG. 2.

The detector 40 can be disposed within the housing 12 of the device 10 in any suitable location. In one or more embodiments, the detector 40 is disposed along the optical axis 31. Further, in one or more embodiments, the detector 40 can be disposed along the optical axis 31 such that a center 46 of the input surface 42 is disposed on the optical axis (as shown in FIG. 4). The detector 40 can be disposed within the housing 12 such that the input surface 42 forms any suitable angle with the optical axis 31. In one or more embodiments, the input surface 42 can be substantially orthogonal to the optical axis. As used herein, the phrase "substantially orthogonal" means that the input surface 42 forms an angle with the optical axis 31 that is at least 85° and no greater than 95°.

The detector 40 can be disposed within the housing 12 such that the input surface 42 of the detector is adjacent the second end 36 of the receptacle body 32. As used herein, the phrase "adjacent the second end" means that the input surface 42 of the detector 40 is disposed next to the second end 36 of the receptacle body 32 such that the input surface can receive light emitted by a sample disposed within the receptacle 30. The input surface 42 of the detector 40 can be disposed at any suitable distance from the second end 36 of the receptacle body 32. In one or more embodiments, the distance between the input surface 42 and the second end 36 of the receptacle body 32 can be adjustable.

Figure 5:
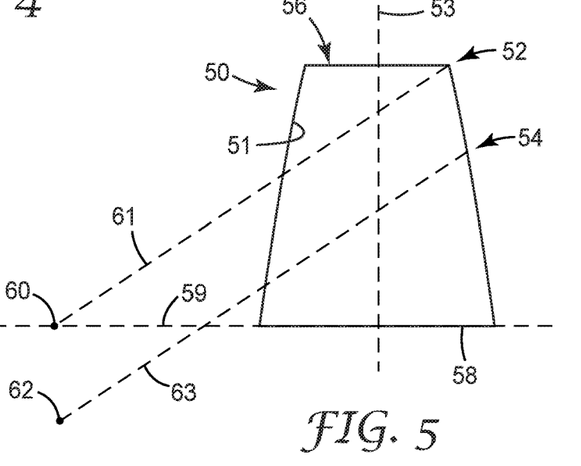
FIG. 5 is a schematic cross-section view of a reflector of the light detection device of FIG. 2.

The light detection device 10 can also include a reflector 50 disposed within the housing 12 along the optical axis 31 between the second end 36 of the receptacle body 32 and the input surface 42 of the detector 40. The reflector 50 can include an input aperture 56, an output aperture 58, and a reflective surface 51 that extends between the input aperture and the output aperture (FIG. 5). The input aperture 56 can be disposed adjacent the second end 36 of the receptacle body 32. As used herein, the phrase "adjacent the second end" means that the input aperture 56 is disposed closer to the second end 36 of the receptacle body 32 than to the input surface 42 of the detector 40. And the output aperture 58 can be disposed adjacent the input surface 42 of the detector 40. As used herein, the phrase "adjacent the input surface" means that the output aperture 58 is disposed closer to the input surface 42 than to the second end 36 of the receptacle body 32. The reflective surface 51 can have any suitable cross-sectional shape or combination of shapes in a plane orthogonal to the reflector axis 53, e.g., circular, elliptical, polygonal, etc. In one or more embodiments, the reflective surface 51 can have a first cross-sectional shape and one or more additional cross-sectional shapes. For example, the reflective surface 51 can have a circular cross-sectional shape at the input aperture 56 and a rectangular cross-sectional shape at the output aperture 58, and the reflective surface can be adapted to transition from the circular cross-sectional shape to the rectangular cross-sectional shape.

The input aperture 56 can have any suitable diameter in a plane orthogonal to the reflector axis 53. For example, in one or more embodiments, the diameter of the input aperture 56 can be at least about 5 mm. Further, in one or more embodiments, the diameter of the input aperture 56 can be no greater than about 25 mm. In general, the input aperture 56 is sized to accommodate a cuvette portion of a sampling apparatus and/or the transmissive region 38 of the receptacle body 32. The input aperture 56 can have any suitable cross-sectional area in a plane orthogonal to the reflector axis 53. For example, in one or more embodiments, the input aperture 56 can have a cross-sectional area of at least 15 mm$^2$. In one or more embodiments, the input aperture can have a cross-sectional area of no greater than 500 mm$^2$.

The output aperture 58 can also have any suitable diameter in a plane orthogonal to the reflector axis 53. For example, in one or more embodiments, the diameter of the output aperture 58 can be at least about 5 mm. Further, in one or more embodiments, the diameter of the output aperture 58 can be no greater than about 50 mm. The output aperture 58 can have any suitable cross-sectional area in a plane orthogonal to the reflector axis 53. In one or more embodiments, the output aperture 58 can have a cross-sectional area of at least 15 mm$^2$. In one or more embodiments, the output aperture 58 can have a cross-sectional area of no greater than 2000 mm$^2$.

In general, the output aperture 58 is sized to accommodate the active area of the input surface 42 of the detector 40. In one or more embodiments, the cross-sectional area of the output aperture 58 is no greater than the active area of the input surface 42 of the detector 40. In one or more embodiments, the active area of the input surface 42 of the detector 40 is surrounded by the output aperture 58 of the reflector 50. Further, in one or more embodiments, the cross-sectional area of the output aperture 58 can be less than the active area of the input surface 42. For example, the cross-sectional area of the output aperture 58 can be about 10%, 5%, 4%, 3%, 2%, 1% smaller than the active area of the input surface 42. In one or more embodiments, the cross-sectional area of the output aperture 58 can be in a range of 1-10% smaller than the active area of the input surface 42. In one or more embodiments, the cross-sectional area of the output aperture 58 can be in a range of 1-5% smaller than the active area of the input surface 42.

The cross-sectional area of the output aperture 58 of the reflector 50 can be any suitable size relative to the cross-sectional area of the input aperture 56. In one or more embodiments, the cross-sectional area of the output aperture 58 is greater than the cross-sectional area of the input aperture 56. In one or more embodiments, the cross-sectional area of the output aperture 58 is at least 1.5 times greater than the cross-sectional area of the input aperture 56. In one or more embodiments, the cross-sectional area of the output aperture 58 is at least 2 times greater than the cross-sectional area of the input aperture 56. In one or more embodiments, the cross-sectional area of the output aperture 58 is at most 70 times greater than the cross-sectional area of the input aperture 56.

The reflector 50 can have any suitable length between the input aperture 56 and the output aperture 58 as measured along the reflector axis 53. In one or more embodiments, the length of the reflector 50 can be at least about 10 mm, at least about 12 mm, at least about 15 mm, at least about 20 mm, at least about 30 mm, etc. In one or more embodiments, the length of the reflector 50 can be no greater than about 50 mm.

The reflector 50 can be disposed in any suitable relationship to the active area of the input surface 42 of the detector 40. In one or more embodiments, the input aperture 56, the output aperture 58, and the active area of the input surface 42 can be centered along the optical axis 31.

The reflector 50 can be disposed such that the reflective surface 51 surrounds at least a portion of the transmissive region 38 of the receptacle body 32. In one or more embodiments, the reflector 50 can be disposed such that reflective surface 51 surrounds the entire transmissive region 38. In one or more embodiments, the reflector 50 can be disposed such that the reflective surface 51 surrounds only a portion of the transmissive region 38. In one or more embodiments, the reflective surface 51 can be shaped such that it encloses the transmissive region 38 within a volume defined by the input aperture 56, the output aperture 58, and the reflective surface. Further, in one or more embodiments, a portion of the transmissive region 38 can be disposed outside of this volume. In one or more embodiments, the entire transmissive region 38 can be disposed within this volume.

The reflective surface 51 and the input surface 42 of the detector 40 can together form a light cavity 44. The light cavity 44 can be hollow. In one or more embodiments, the light cavity 44 can be a solid lightguide with the transmissive region 38 of the receptacle body 32 disposed within the solid lightguide.

The reflector 50 can be adapted such that any suitable percentage of light emitted into the light cavity 44 by a sample disposed within the receptacle 30 is directed through the input surface 42 of the detector 40 within the active area. As used herein, the phrase "through the input surface 42 of the detector 40" means that light incident upon the input surface of the detector within the active area is at an angle with a normal vector to the input surface that is within an acceptance angle of the detector. The acceptance angle of the detector 40 is an angle at which light that is incident upon the input surface 42 within the active area is directed through the input surface and into the detector to be detected. In other words, light that is incident upon the input surface 42 of the detector 40 such that it is reflected at the surface and is not directed into the detector is outside of the acceptance angle of the detector. In one or more embodiments, at least 15% of the light emitted into the light cavity 44 by the sample is directed through the input surface 42 of the detector 40. In one or more embodiments, at least 20% of the light emitted into the light cavity 44 by the sample is directed through the input surface 42 of the detector 40. In one or more embodiments, at least 50% of the light emitted into the light cavity 44 by the sample is directed through the input surface 42 of the detector 40.

The reflective surface 51 can take any suitable shape or combination of shapes such that the reflector 50 directs at least a portion of the emitted light through the input surface 42 within the active area. In general, a reflector having a parabolic shape rotated around a point source, e.g., a compound parabolic concentrator, will redirect light emitted by the point source disposed at a focal point of the reflector as parallel rays at an output aperture of the reflector. In reference to a sample apparatus as described herein, light can be emitted by a sample through the transmissive region 38 of the receptacle body 32, thereby providing a larger radiating surface than that of a point source. In one or more embodiments, the reflective surface 51 can be substantially cylindrical. In other words, the reflective surface 51 can be formed such that it has sides that are substantially parallel to a center axis 53 of the reflector (FIG. 5). In one or more embodiments, the reflective surface 51 can take a parabolic shape, e.g., a parabolic curve can be rotated about the reflector axis 53 to provide a parabolic shaped reflector.

The reflective surface 51 can include a first portion 52 that has a first radius of curvature 61 as shown in FIG. 5. In one or more embodiments, the entire reflective surface 51 has the first radius of curvature 61. As illustrated in FIG. 5, the first radius of curvature 61 is centered at center 60. The center 60 of the first radius of curvature 61 can be located in any suitable location relative to the reflector 50. For example, in one or more embodiments, the center 60 of the first radius of curvature 61 can be disposed on a plane 59 that is defined by the output aperture 58 of the reflector 50. In one or more embodiments, the center 60 of the first radius of curvature 61 can be located or disposed below the plane 59, i.e., the center 60 can be disposed such that the plane 59 is between the center 60 and the input aperture 56 of the reflector 50.

In one or more embodiments, the reflective surface 51 of reflector 50 can include any suitable number of radii of curvature. For example, as illustrated in FIG. 5, the reflective surface 51 includes a second portion 54 that has a second radius of curvature 63 centered at center 62. The second radius of curvature 63 can be the same as the first radius of curvature 61. In one or more embodiments, the second radius of curvature 63 is different from the first radius of curvature 61. Center 62 of the second radius of curvature 63 can be located in any suitable location relative to the reflector 50. For example, in one or more embodiments, the second radius of curvature can be located on the plane 59. In one or more embodiments, the center 62 of the second radius of curvature 63 can be located below the plane 59, i.e., the center 62 of the second radius of curvature 63 is disposed such that the plane 59 is between the center 62 and the input aperture 56 of the reflector 50. In one or more embodiments, centers 60, 62 can be disposed on plane 59. In one or more embodiments, one or both of the centers 60, 62 can be disposed below the plane 59.

Although reflector 50 is depicted as having first and second portions 52, 54 having different radii of curvature, the reflective surface 51 can include three or more portions that have different radii of curvature. Further, in one or more embodiments, a suitable number of portions of the reflective surface 51 of reflector 50 can include the first radius of curvature 61 or the second radius of curvature 63.

The first and second radii of curvature 61, 63 can each include any suitable length. In one or more embodiments, one or both of the first and second radii of curvature 61, 63 can have a radius of at least about 50 mm, 55 mm, 60 mm, 65 mm, 70 mm, 100 mm, 200 mm, 500 mm, 600 mm, 700 mm, etc. Further, in one or more embodiments, one or both of the first and second radii of curvature 6163 can have a radius of no greater than about 800 mm.

The reflector 50 can be disposed within the housing 12 of the device 10 in any suitable location. In one or more embodiments, the reflector 50 can be disposed along the optical axis 31. Further, in one or more embodiments, the reflector axis 53 can be substantially aligned with the optical axis 31. In one or more embodiments, the reflector axis 53 can be collinear with the optical axis 31 such that the reflector 50 is centered along the optical axis.

The first portion 52 having the first radius of curvature 61 can be disposed in any suitable relationship relative to the second portion 54 having the second radius of curvature 63. In one or more embodiments, the first portion 52 is adjacent the second portion 54. In one or more embodiments, a portion of the first portion 52 intersects or overlays a portion of the second portion 54. In one or more embodiments, the first portion 52 is adjacent the second portion 54 such that the curvature of the reflective surface 51 is continuous, i.e., the first portion transitions into the second portion 54 without an inflection between the two portions. In one or more embodiments, a flat portion can be disposed between the first portion 52 and the second portion 54. Further, in one or more embodiments, a ridge, step, or facet can be disposed between the first portion 52 and the second portion 54.

In one or more embodiments, the reflective surface 51 of reflector 50 can be adapted such that light emitted into the light cavity 44 by the sample is directed through the input surface 42 of the detector 40 within the active area after being incident upon the reflective surface any suitable number of times. For example, in one or more embodiments, at least a portion of light emitted into the light cavity 44 is directed through the input surface 42 within the active area after no more than, e.g., 10 reflections from the reflective surface 51 of the reflector 50. In one or more embodiments, at least a portion of light emitted into the light cavity 44 is directed through the input surface 42 within the active area after no more than one reflection from the reflective surface 51 of the reflector 50. In one or more embodiments, at least a portion of light emitted into the light cavity 44 is directed through the input surface 42 within the active area without being reflected or being incident upon the reflective surface 51. Any suitable percentage of the light emitted into the light cavity 44 can be directed through the input surface 42 within the active area after being reflected at most one time by the reflective surface 51, i.e., with at most one reflection, e.g., at least 10% at least 20%, at least 30%, at least 40%, at least 50%, at least 60%, at least 70%. Any suitable technique or combination of techniques can be utilized to determine the percentage of light emitted into the light cavity 44 by the sample that is directed through the input surface 42 within the active area after being reflected at most one time by the reflective surface 51, e.g., the reflector and light cavity 44 can be modeled using any suitable ray tracing software program such as TracePro (Lambda Research Corporation, Littleton, Mass.).

The reflector 50 can include any suitable material or combination of materials such that the reflector is reflective, e.g., metallic, polymeric, etc. In one or more embodiments, the reflector 50 includes a multilayer optical film. Any suitable multilayer optical film or combination of films can be utilized, e.g., Vikuiti™ Enhanced Specular Reflector Film (ESR) (available from 3M Company, St. Paul, Minn.). The multilayer optical film can be disposed on a shaped substrate to provide the reflective surface 51 of reflector 50. In one or more embodiments, the multilayer optical film can be formed into a desired shape or combination of shapes to provide the reflective surface 51. For example, in one or more embodiments, the multilayer optical film can be thermoformed to provide a desired shape for the reflective surface 51.

The reflective surface 51 can provide any suitable reflective properties. For example, at least a portion of the reflective surface 51 can be a specularly reflective surface. In one or more embodiments, at least a portion of the reflective surface 51 can be a diffusely reflective surface. The reflector 50, therefore, can be a specular reflector, a diffuse reflector, or a combination specular/diffuse reflector.

The device 10 can also include any additional optical element or elements that are adapted to enhance the accuracy of the detector 40. For example, in one or more embodiments, a mask (not shown) can be disposed adjacent the input surface 42 of the detector 40. As used herein, the phrase "disposed adjacent the input surface" means that the mask is disposed such that it is closer to the input surface 42 of the detector 40 then to the input aperture 56 of the reflector 50. The mask can be a separate element that is disposed adjacent the input surface 42 of the detector 40. In one or more embodiments, the mask can be formed such that it is integral with the reflector 50. In one or more embodiments, the mask can be disposed on the input surface 42. In such embodiments, the mask can be attached to the input surface 42 using any suitable technique or combination of techniques. In embodiments where the mask is a part of the reflector 50, the mask can be attached to the input surface 42 of the detector 40 to seal the reflector to the input surface, thereby preventing light emitted into the light cavity 44 by the sample from being transmitted out of the light cavity before being transmitted through the input surface 42. In embodiments where a mask is not included, the reflector 50 can be attached to the input surface 42 of the lightguide using any suitable technique or combination of techniques such that light emitted into the light cavity 44 does not escape the cavity, e.g., the light cavity is sealed to prevent light leakage.

The reflector 50 can be disposed in any suitable relationship relative to the detector 40. For example, the output aperture 58 of the reflector 50 can be spaced apart from the input surface 42 of the detector 40 any suitable distance, e.g., no greater than 30 mm, no greater than 25 mm, no greater than 20 mm, no greater than 10 mm, greater than 5 mm, no greater than 1 mm, no greater than 0.5 mm, etc. In one or more embodiments, a portion of the reflector 50 at the output aperture 58 can be in contact with the input surface 42 of the detector 40. Further, the reflector 50 can be connected to the detector 40 using any suitable technique or combination of techniques. For example, the reflector 50 can include ledges 66 that can be in contact with one or both of the input surface 42 and sides of the detector 40 (FIG. 4). In one or more embodiments, the reflector 50 and the detector 40 can be held in place using any suitable technique or combination of techniques such that the reflector does not move relative to the detector.

The device 10 can also include a light source 70 that is adapted to emit light into the light cavity 44. In one or more embodiments, the light source 70 can be utilized as a reference source that can help determine an analog counting level of the detector 40. Reference light from the light source 70 can be directed into the light cavity 44 through an opening formed in the reflector 50 as shown in FIG. 4. The opening can take any suitable shape and have any suitable dimensions. In one or more embodiments, the opening can be a pin-hole opening. Light source 70 can be electrically coupled to circuitry 28 disposed within the housing 12 of the device 10. In one or more embodiments, the device 10 can include a feedback loop that can be utilized to control the light source 70 based upon the output of the detector 40 in response to the light source. The light source 70 can include any suitable light source, e.g., one or more light emitting diodes.

Light source 70 can be disposed such that an emission axis 72 of the light source forms any suitable angle with the optical axis 31. As used herein, the term "emission axis" refers to an axis of a light source along which the light source emits a maximum intensity of light. In one or more embodiments, the emission axis 72 of the light source 70 intersects the center 46 of the active area of the input surface 42 of the detector 40. Further, in one or more embodiments, the emission axis 72 is not parallel to the optical axis 31. In one or more embodiments, a diffuser (not shown) can be disposed between the light source 70 and the input surface 42 of the detector 40 to provide a more uniform light distribution from the light source into the light cavity 44.

Figure 6:
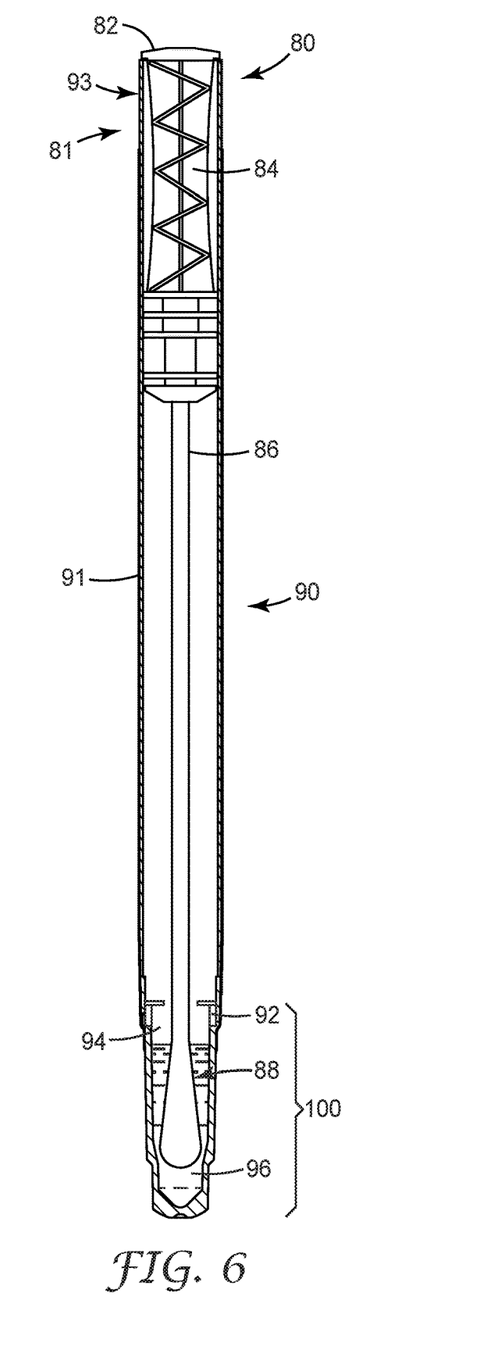
FIG. 6 is a schematic cross-section view of one embodiment of a sampling apparatus.

In one or more embodiments, a sample or samples of material to be tested can be disposed directly in the receptacle 30. In one or more embodiments, the sample can be disposed in a sampling apparatus that is disposed in the receptacle 30. Any suitable sampling apparatus can be utilized with system 2, e.g., the sampling apparatuses described in PCT Patent Publication No. WO 2014/007846 and U.S. Patent Publication No. 2012/0329081. For example, FIG. 6 is a schematic cross-section view of one embodiment of a sampling apparatus 80. The sampling apparatus 80 includes a sampling device 81 and a container 90. The sampling device 81 can include any suitable sampling device. The sampling device 81 includes a handle portion 82 that includes a handle 84 and a sampling portion 88. The sampling portion 88 can be coupled to the handling portion 82 via an optional stem 86. The sampling device 81 can be shaped and dimensioned to be received in the container 90. The handling portion 82 can include any suitable material or combination of materials and can function as a location at which the sampling device 81 can be grasped and/or manipulated during use. The handle 84 can be shaped and/or textured to facilitate manual or mechanical gripping of the sampling device 81.

The sampling portion 88 can include any suitable material or combination of materials capable of obtaining and retaining a sample from a sample source. In one or more embodiments, the sampling portion can retain a sample collected from an environmental surface, e.g., surfaces found in a food processing plant and food processing equipment, and surfaces found in a hospital including high touch surfaces in a patient room or an operating room and the surfaces of medical devices including surgical instruments and rigid and flexible endoscopes. In one or more embodiments, the sampling portion 88 can retain a liquid sample, e.g., liquids used in food processing operations including testing water quality, sterile water used to harvest samples from the inner surfaces of lumened and cannulated surgical instruments and other medical devices, and water used in medical procedures such as dialysis and endoscopy. In one or more embodiments, the sampling device 81 can include a coating, e.g., on the sampling portion 88, such that when the device is disposed in or comes in contact with a sample the coating is contacted with the sample. Any suitable coating or combination of coatings can be included with the sampling device 81.

The container 90 can include at least one wall 91 and an opening 93 adapted to receive the sampling device 81. In one or more embodiments, the container 90 can be adapted to receive the entire sampling device 81. The container 90 can also include a cuvette portion 100 adapted to be operationally coupled to a light detection device, e.g., light detection device 10. In one or more embodiments, the cuvette portion 100 is operationally coupled to a light detection device by placing the cuvette portion of the container 90, or the entire container, into a complimentary shaped receiving compartment of the light detection device, e.g., receptacle 30 of system 2.

The cuvette portion 100 can include any suitable material or combination of materials. In one or more embodiments, the cuvette portion 90 includes material or combination of materials that provide an optically transmissive region that permits the transmission therethrough of light emitted as a product of a reaction catalyzed within the sampling device 81, e.g., light emitted as a product of a reaction catalyzed by a luciferase enzyme.

A reagent composition 96 can be disposed within the container 90. The reagent composition 96 can be a liquid, gas, or solid reagent. The reagent composition 96 can include any suitable reagent or combination of reagents, e.g., luciferin/luciferase ATP detecting reagents, ninhydrin, and bicinchoninic acid protein detecting reagents.

The reagent composition 96 can be disposed in a closed compartment 94 of the container 90 formed by a frangible wall 92 disposed adjacent the cuvette portion 100. The frangible wall 92 can include any suitable material or combination materials. In one or more embodiments, the frangible wall 92 can be made from a water resistant material, e.g., a plastic film, metal foil, or a metal coated plastic film. The frangible wall 92 can be attached to the cuvette portion 100 and/or the wall 91 of the container 90 using any suitable technique or combination of techniques, e.g., an adhesive, a heat seal, a sonic weld, etc.

In general, a light detection system can be used to detect the presence or absence, e.g., of ATP in a liquid sample using any suitable technique or combination of techniques. The presence of ATP in a sample can indicate a possible presence of organic residues and/or microorganisms (e.g., pathogenic microorganisms) in a sample. In one or more embodiments, the quantity of ATP in the sample can be an indicator of the relative number of microorganisms in the sample.

For example, the sampling apparatus 80 can be utilized to obtain a predetermined volume of a liquid sample. The sampling device 81 can be used to contact the predetermined volume of sample with a liquid reagent composition 96 in the container 90 to form a reaction mixture. The sampling apparatus can then be utilized with a light detection device, e.g., light detection device 10, to detect light emitted from the reaction mixture.

In one or more embodiments, the sampling apparatus 80 can be utilized to detect ATP that is present in residue on a surface, e.g., liquid and/or solid residue found on a solid surface. For example, the sampling apparatus 80 can be utilized to detect the efficacy of a process that is used to clean the surface. In many environments (e.g., food processing facilities, hospitals), the cleaning process should substantially reduce or remove detectable ATP from the surface that is to be tested. Suitable samples that can be tested utilizing sampling apparatus 80 include processing equipment (e.g., food handling surfaces, tubes, drains, conveyors, storage containers), environmental surfaces (e.g., sinks, countertops, drawers, floors, walls, ceilings, doors, bed rails, linens, computer touchscreens, keyboards, monitors), and medical equipment or devices (e.g., endoscopes, retractors, trocars, scalpels, trays). Such samples can include liquid and/or solid residue present on a surface.

In one or more embodiments, a sample can be obtained using the sampling device 81. Sampling device 81 is inserted into the container 90. Using manual or mechanical pressure against the handle 84 of the sampling device 81, sampling portion 88 is urged toward the compartment 94 until it ruptures the frangible wall 92 and brings the liquid sample (not shown) associated with the sampling portion 88 into contact with the reagent composition 96 as is shown in FIG. 6. The sampling device 81 and the container 90 are disposed in an operational position with respect to each other. In one or more embodiments, the sampling device 81 is fully inserted into the container 90 and the sampling portion 88 of the sampling device contacts the reagent composition 96.

A bioluminescent sample can be disposed within the receptacle 30 of light detection device 10 by placing the sampling apparatus 80 within the receptacle 30. The door 11 can be opened and the sampling apparatus can be inserted into the opening 21 of the port 20 of housing 12 of the detection device 10. The sampling apparatus 80 can be inserted into the receptacle 30 until at least a portion of the cuvette portion 100 is disposed within the light cavity 44 either on its own or within the optional transmissive region 38 of the receptacle body 32. The cuvette portion 100 may be operationally coupled to the light detection device 10 before or after forming the reaction mixture. As used herein, the term "operationally coupled" means that the cuvette portion 100 is disposed within the housing 12 such that at least a portion of light that may be emitted by the sample can be directed through the input surface 42 within the active area. In one or more embodiments, the cuvette portion 100 is operationally coupled to the light detection device 10 after the reaction mixture is formed. In one or more embodiments, the cuvette portion 100 is operationally coupled to the light detection device for any suitable length of time to provide an optical signal, e.g., at least 1 second, 5 seconds, 10 seconds, 15 seconds, 20 seconds, 30 seconds, 60 seconds, 2 minutes, 5 minutes, 10 minutes, 15 minutes, 20 minutes, etc.

After the sampling apparatus 80 is disposed within the receptacle 30 of light detection device 10 such that the cuvette portion 100 of the sampling apparatus is operationally coupled to the device, the light emission is monitored by the device. At least a portion of light that may be emitted by the sample is transmitted into the light cavity 44. A first portion of this transmitted light may be directed through the input surface 42 of the detector 40 within the active area without either being reflected by reflector 50 or being absorbed by the sample. A second portion of light emitted into the light cavity 44 can be directed through the input surface 42 within the active area by being reflected by the reflective surface 51 of reflector 50.

One or more characteristics of the emitted light can be measured using the detector 40. For example, the detector 40 can be utilized to detect one or more photons that may have been emitted by the sample that is disposed within the receptacle 30. In one or more embodiments, the detection device 10 can detect light emitted from the reaction mixture and measure a selected quantity or quantities (e.g., a relative quantity or an absolute quantity of ATP present in the sample). This light output can be quantified by the light detection device 10. The presence of ATP in a sample may be a direct indicator of the presence of a microorganism (i.e., the ATP is derived from a microorganisms in a sample containing no other sources of ATP) or the ATP may be an indirect indicator of the presence of a microorganism (i.e., the ATP is derived from vegetative or animal matter and indicates that nutrients that support the growth of microorganisms may be present in the sample).

When measuring light emitted by a sample using a light detection device (e.g., light detection device 10), the angle at which the device is held or positioned during detection of the emitted light can affect the accuracy of the device. Measuring a sample with an instrument not held at the appropriate angle can yield a measured value difference greater than 20% relative to the real value. This is because the sample being measured can typically be a small volume (less than 1 mL) liquid sample disposed in a cuvette portion of the sampling apparatus (e.g., cuvette portion 100 of apparatus 80) that can have an appreciable meniscus. When the instrument is held in an improper angle, at least a portion of the sample can be disposed outside of the light cavity of the detection device (e.g., light cavity 44 of device 10) of the system, thereby reducing a volume of the sample that can emit light into the light cavity and, therefore, potentially yielding an erroneous signal. The total bioluminescence radiance is emitted from both the bulk solution and the sampling portion of the sampling device (e.g., sampling portion 88 of device 81). This tilt can affect the radiance of the sample being analyzed.

In one or more embodiments, the detection device 10 can also include a tilt detection component (not shown) that can, in one or more embodiments, measure a tilt angle of the detection device 10. As used herein, the term "tilt angle" means an angle formed between the housing axis 4 and a vertical axis. As used herein, the term "vertical axis" refers to an axis that is aligned with the Earth's gravitational field. The tilt detection component can provide feedback to a user when the device 10 is positioned within a proper tilt angle and/or when the device is positioned at an improper tilt angle. Such feedback can be provided to the user using any suitable technique or combination of techniques, e.g., the feedback can be provided as a readout on the display 24, or the device 10 can be adapted to provide haptic feedback to the user. For example, during detection of light emitted by a sample, the user can be warned by an on-screen message on display 24, or the device 10 can provide haptic feedback, when the instrument is not being held at the correct tilt angle and/or when the instrument is being held at the correct tilt angle. On-screen instructions can be provided to the user to reorient the device 10 such that it is positioned within the correct tilt angle. The tilt detection component can be utilized to indicate to a user any suitable tilt angle or range of tilt angles. In one or more embodiments, a desirable tilt angle can be determined, e.g., by the quantity of a sample disposed within the housing, and by the optical properties and configurations of the detector within the housing. In general, the tilt angle can be selected to provide the most accurate detection of one or more characteristics of a sample disposed within the housing.

The tilt detection component can include any suitable circuitry or elements that can determine an orientation of the device 10 relative to the vertical axis. For example, in one or more embodiments, the tilt angle can be measured by a tilt sensor that is sampled by a microprocessor disposed either within the housing 12 of the device 10 or external to the housing 10 and coupled to the tilt sensor either wirelessly or through a wired coupling. Data provided by the tilt sensor can be averaged or normalized to yield a stable approximation of the tilt angle of the device 10 prior to or during analysis of the sample. The tilt detection component can be calibrated to have any suitable accuracy. For example, in one or more embodiments, the tilt detection component can be calibrated such that it provides, e.g., a 20% tilt angle measurement accuracy.

While not wishing to be bound by any particular theory, measuring a sample with an instrument not held at the appropriate angle can yield a measured value difference greater than 20% relative to the real value because the sample being measured can typically be a small volume (less than 1 mL) liquid sample disposed in a cuvette portion of the sampling apparatus, where the sample can have an appreciable meniscus. When the device is held in an improper angle, at least a portion of the sample can be disposed outside of a light cavity of the detection device of the system that directs light to a detector, thereby reducing a volume of the sample that can emit light into the light cavity and, therefore, potentially yielding an erroneous signal. This tilt can, therefore, affect the radiance of the sample being analyzed.

In one or more embodiments, the tilt detection component can also be utilized to measure customer usage behaviors and abuse events that can be useful in predicting desired service intervals or provide training and guidance. Further, one or more embodiments of the tilt detection component can provide real-time mathematical normalization of RLU data based on measured tilt angle. This algorithm may be constrained to practical tilt angle limits. For example, measured angles greater than 90 degrees would prompt an immediate warning and suppress a normalization algorithm. In one or more embodiments, providing a user feedback on the tilt angle can allow the user to maintain the same tilt angle across multiple samples, thereby allowing for more consistent readings from sample to sample and from sampling period to sampling period.

Any suitable technique or combination of techniques can be utilized to maintain the light detection device 10 in a position having the appropriate tilt angle. For example, in one or more embodiments, a support member or members can be connected to the housing 12 of the device 10 such that the device can be placed on a work surface such that the device sits on the work surface at the desired tilt angle. Any suitable support member or members can be connected to the housing 12, e.g., the support members described in co-filed U.S. Provisional Patent Application Ser. No. 61/132,794, filed Mar. 13, 2015.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A light detection device, comprising:
    a housing extending along a housing axis between a top surface and a bottom surface, wherein the housing comprises a port disposed in the top surface, wherein the port comprises an opening;
    a receptacle disposed within the housing and adapted to receive a sample, wherein the receptacle comprises a receptacle body extending along an optical axis, the receptacle body comprising a first end connected to the opening of the port of the housing and a second end;
    a detector disposed within the housing along the optical axis and comprising an input surface adjacent the second end of the receptacle body, wherein the input surface comprises an active area; and
    a reflector disposed within the housing along the optical axis between the second end of the receptacle body and the input surface of the detector, wherein the reflector comprises an input aperture having a cross-sectional area and being disposed adjacent the second end of the receptacle body, an output aperture having a cross-sectional area and being disposed adjacent the input surface of the detector, and a reflective surface that extends between the input aperture and the output aperture;
    wherein the cross-sectional area of the output aperture of the reflector is at least 2 times greater than the cross-sectional area of the input aperture and at most 70 times greater than the cross-sectional area of the input aperture.

2. The device of claim 1, wherein the receptacle further comprises a shutter disposed within the receptacle body between the first end and the second end of the body, wherein the shutter is adapted to prevent at least a portion of ambient light that enters the housing through the port from being transmitted through the active area of the input surface of the detector when the sample is not disposed within the receptacle.

3. The device of claim 1, wherein the reflector comprises a multilayer optical film.

4. The device of claim 1, wherein a portion of the reflector at the output aperture is in contact with the input surface of the detector.

5. The device of claim 1, wherein the active area of the input surface of the detector is aligned with the optical axis such that optical axis intersects a center of the active area.

6. The device of claim 1, wherein the active area of the input surface of the detector is surrounded by the output aperture of the reflector.

7. The device of claim 1, wherein the reflector and the input surface of the detector form a light cavity.

8. The device of claim 7, wherein the receptacle further comprises a transmissive region adjacent the second end of the receptacle body, wherein at least a portion of the transmissive region is disposed within the light cavity; and further
    wherein the transmissive region comprises a transmissive cup that is connected to the second end of the receptacle body.

9. The device of claim 7, further comprising a light source adapted to emit light into the light cavity.

10. The device of claim 9, wherein an emission axis of the light source intersects a center of the active area of the input surface of the detector.

11. The device of claim 10, wherein the emission axis of the light source is not parallel to the optical axis.

12. The device of claim 1, wherein the detector comprises a photomultiplier tube, a photodiode, or both.

13. The device of claim 1 wherein the optical axis is parallel to the housing axis.

14. The device of claim 1, wherein the input surface of the detector is orthogonal to the optical axis.

15. The device of claim 1, wherein the input aperture, output aperture, and active area of the input surface of the detector are centered along the optical axis.

16. The device of claim 1, further comprising a tilt detection component adapted to determine an angle formed between the housing axis and a vertical axis.

17. A light detection system comprising a sampling apparatus and the light detection device of claim 1, wherein the sampling apparatus comprises:
    a container comprising an opening and a cuvette portion that is adapted to be operationally coupled to the detector;
    a sampling device comprising a sampling portion, wherein the sampling portion is adapted to acquire and releasably retain the sample; and
    wherein the receptacle is adapted to receive the sampling apparatus.

18. The system of claim 1, wherein the reflector and the input surface of the detector form a light cavity, and wherein the input aperture of the reflector is adapted to receive the cuvette portion of the sampling apparatus such that at least a portion of the cuvette portion is disposed within the light cavity when the sampling apparatus is disposed within the receptacle.

19. A method, comprising:
    disposing a bioluminescent sample within a receptacle of a light detection device of claim 1,
    directing light emitted into the light cavity by the bioluminescent; and
    measuring a characteristic of the emitted light using the detector.

* * * * *